United States Patent [19]
Gentle, Jr. et al.

[11] Patent Number: 5,998,517
[45] Date of Patent: Dec. 7, 1999

[54] COMPOSITION FOR THE DETECTION OF MICROORGANISMS IN A SAMPLE

[75] Inventors: Thomas M. Gentle, Jr., Red Lion; Ming-Hsiung Yeh, New Freedom, both of Pa.

[73] Assignee: Becton, Dickinson and Company, Franklin Lakes, N.J.

[21] Appl. No.: 09/092,689

[22] Filed: Jun. 5, 1998

[51] Int. Cl.⁶ ..................................... C08K 5/34
[52] U.S. Cl. ............................ 524/92; 523/122; 524/176
[58] Field of Search ...................... 524/92, 176; 523/122

[56] References Cited

U.S. PATENT DOCUMENTS 4,022,751  5/1977  Johnson ........................... 260/44.75 N
4,396,734  8/1983  Williams et al. ......................... 524/89
5,670,611  9/1997  Baardman et al. ....................... 528/392

*Primary Examiner*—Edward J. Cain
*Attorney, Agent, or Firm*—Bruce S. Weintraub

[57] ABSTRACT

The present invention relates to a composition for the detection of the growth of respiring microorganisms in a sample, which comprises:
(a) tris(4,7-diphenyl-10-phenanthroline)ruthenium dichloride pentahydrate;
(b) a hydroxyl functional group;
(c) an organosilicon polymer;
(d) an organohydrogensilicon compound; and
(e) a catalyst;
and a method for preparing said composition.

20 Claims, No Drawings

COMPOSITION FOR THE DETECTION OF MICROORGANISMS IN A SAMPLE

BACKGROUND OF THE INVENTION

The earth's environment contains a multitude of microorganisms with which we are continuously interacting. The interactions can be beneficial, e.g. fermentations to produce wine, vinegar or antibiotics, neutral or even harmful as in the case of infectious diseases. The widespread presence of these microorganisms creates a continuing need for the detection, identification and study of their metabolic activity.

While the science of microbiology has changed significantly in the last quarter century, many procedures utilized for the detection, identification and analysis of the behavior of microorganisms are still time-consuming. For example, in the area of antimicrobic susceptibility, many of the hospitals in the United States still use tests which rely on the presence or absence of visible growth of microorganisms to indicate the efficacy of an antimicrobic compound. The most common of such tests is the Bauer-Kirby Disc Method which generally requires an 18 to 24 hour incubation period to allow for microorganism growth before a result can be obtained.

Another method of testing for antimicrobic susceptibility is the broth micro-dilution method, such as the Sceptor® System for identification and antimicrobic susceptibility testing of organisms (Becton Dickinson Diagnostic Instrumentation Systems, Sparks, Md.). The system uses a disposable plastic panel having a plurality of low volume cupulas (ca. 0.4 ml per cupula), each containing a different test compound or a different concentration of a test compound dried on the cupula surface. The organism to be tested is suspended in the desired testing medium, and aliquots are delivered to the individual cupulas of the test panel. The reagent dried on the panel dissolves in the sample, and the system is then incubated overnight (18 to 24 hours) to allow sufficient time for the organisms to interact with the reagent and for visible growth to appear. The panel is subsequently examined visually for the presence or absence of growth, thereby obtaining information on the susceptibility of the organism undergoing testing. Additional wells aid in identifying the organism. However, as indicated, this test method requires a long incubation period.

One approach to solving the requirement of long incubation periods is to monitor metabolic activity of the microorganisms rather than the growth of colonies. The growth of organisms in blood culture media can be monitored by a variety of methods such as detecting changes in turbidity, in pressure in a sealed culture vial, incorporation of radioactive substrates into metabolic products such as carbon dioxide, measuring the production of carbon dioxide or measuring the consumption of oxygen. As an example, apparatus with light scattering optical means have been used to ascertain susceptibility by determining the change in size or number of microorganisms in the presence of various antimicrobic compounds. Commercial instruments utilizing these principles are exemplified by the Vitec System (BioMerieux Corp.). This system claims to yield information on antimicrobic susceptibility of microorganisms within six hours for many organisms and drug combinations. Other combinations can require as long as 18 hours before the antimicrobic susceptibility of the organism can be determined by this machine.

Since the Bauer-Kirby procedure is still in use, modifications of this procedure have been developed which allow certain samples to be read in four to six hours. However, the modified system is "destructive"in nature, requiring the spraying of a developing solution of a color forming dye onto the test plate. Re-incubation and reading at a later time are, therefore, not possible and if the rapid technique fails, the experiment cannot be continued for a standard evaluation at a later time.

A bioluminescent method based on the quantity of adenosine triphosphate ("ATP") present in multiplying organisms has been described as yielding results of antimicrobic susceptibility testing in four and half hours for certain compositions (Wheat et al.). However, the procedure tends to be cumbersome and broad applicability has not been demonstrated.

Other approaches have involved monitoring microbial oxygen consumption by measuring pH and/or hemoglobin color change, or by using dyes such as triphenyl-tetrazolium chloride and resazurin, which change color in response to the total redox potential of the liquid test medium.

Monitoring the consumption of dissolved oxygen by microorganisms as a marker of their metabolism has been studied for many years. For example, C. E. Clifton monitored the oxygen consumption of microorganisms over a period of several days using a Warburg flask in 1937. This method measured the change in oxygen concentration in a slow and cumbersome manner.

The growth of microorganisms can also be monitored by the fluorescent output of a sensor deposited on the bottom of a blood culture vial, such as in the BACTEC® blood culture analyzer system (Becton Dickinson Diagnostic Instrumentation Systems, Sparks, Md.). Initially, the BACTEC® fluorescent blood culture analyzer system measured the production of carbon dioxide. Later, the BACTEC® system measured the consumption of oxygen.

The BACTEC® systems for measuring both carbon dioxide and oxygen are formulated using a silicone polymer as the sensor matrix to facilitate gas transmission through the sensor. Silicones are used because they are known to have one of the highest gas transmission of any synthetic polymer. The BACTEC® system detects oxygen consumption by the change of fluorescent output of a ruthenium compound having tris-(4,7-diphenyl-1,10-phenanthroline)ruthenium dichloride pentahydrate. This compound emits light (fluorescence) at a wavelength of 620 nanometers (NM) when excited by light at a wavelength of 440 NM. The fluorescence is stopped or quenched in the presence of oxygen. The detection of the microorganism is based on the theory that when a microorganism grows in a sealed culture vial, it will consume or deplete the oxygen inside the vial resulting in an increase in light output which is proportional to microbial growth.

The initial BACTEC® fluorescent blood culture analyzer system was developed by depositing tris-(4,7-diphenyl-1, 10-phenanthroline) ruthenium dichloride pentahydrate from an ethanol solution onto the surface of silica gel. After the ethanol is removed, the resulting powder is compounded into a moisture curable liquid silicone polymer which is then added to a suitable container. Following curing (i.e. the liquid polymer is converted to a solid), culture media and headspace gases (e.g. carbon dioxide, oxygen and nitrogen) are added to the container which is capped.

The present BACTEC® fluorescent blood culture analyzer system requires the deposition of Tris-(4,7-diphenyl-1,10-phenanthroline) ruthenium dichloride pentahydrate from an ethanol solution on a silica gel. The coated silica gel is then mixed with silicone polymer in a heterogenous manner. The sensor thus produced is referred to as a two-phase or heterogeneous sensor. The coated silica gel will precipitate out of the silicone polymer mixture during processing unless mixing is provided. It has not been possible to directly add tris-(4,7-diphenyl-1,10-phenanthroline) ruthenium dichloride pentahydrate to the silicone to produce a functional sensor.

The required steps of depositing tris-(4,7-diphenyl-1,10-phenanthroline) ruthenium dichloride pentahydrate on silica gel from an ethanol solution and expansive mixing to prevent phase separation of coated silica from silicone polymer makes use of the heterogenous sensor expensive and time-consuming and not conducive to large-scale manufacturing.

Therefore, what is lacking in the art, and is now solved by the present invention, is a functional homogenous sensor which does not require the process step of depositing tris-(4,7-diphenyl-1,10-phenanthroline)ruthenium dichloride pentahydrate on silica gel from an ethanol.

SUMMARY OF THE INVENTION

The present invention provides a composition for detecting the growth of respiring microorganisms in a sample which comprises:
(a) tris(4,7-diphenyl-10-phenanthroline)ruthenium dichloride pentahydrate;
(b) a hydroxyl functional organic;
(c) an organosilicon polymer;
(d) an organohydrogensilicon compound; and
(e) a catalyst.

The present invention also provides a composition for detecting the growth of respiring microorganisms in a sample which comprises:
(a) tris(4,7-diphenyl-10-phenanthroline)ruthenium dichloride pentahydrate;
(b) a hydroxyl functional silicone compound
(c) an organosilicon polymer;
(d) an organohydrogensilicon compound; and
(e) a catalyst.

The present invention also provides a method for preparing a composition for detecting the growth of respiring microorganisms in a sample which comprises the steps of:
(i) forming a solution of tris(4,7-diphenyl-10-phenanthroline)ruthenium dichloride pentahydrate and a hydroxyl functional group;
(ii) adding an organosilicon polymer to said solution forming a mixture;
(iii) adding an organohydrogensilicon compound to said mixture in the presence of a catalyst forming an elastomer; and
(iv) adding a filler to said elastomer.

DETAILED DESCRIPTION OF THE INVENTION

The composition of the present invention is a homogenous oxygen sensor that enables the direct addition of tris(4,7-diphenyl-10-phenanthroline) ruthenium dichloride pentahydrate to a liquid silicone polymer by choice of a suitable solvent. The composition changes fluorescence intensity according to the oxygen level in the environment.

Applicants surprisingly discovered that tris(4,7-diphenyl-10-phenanthroline) ruthenium dichloride pentahydrate is soluble in a silanol (a hydroxy group attached to a silicon atom) functional silicone polymer manufactured by Bayer Corporation under the name SI205. Applicants further discovered that a solution of tris (4,7-diphenyl-10-phenanthroline) ruthenium dichloride pentahydrate in SI205 is compatible with silicone polymers. Direct addition of the solution of tris(4,7-diphenyl-10-phenanthroline)ruthenium dichloride pentahydrate in SI205 to silicone polymers resulted in an oxygen sensor capable of detecting the growth of microorganisms in a blood culture. The sensor developed in accordance with the composition of the present invention does not require the deposition of tris(4,7-diphenyl-10-phenanthroline)ruthenium dichloride pentahydrate on a solid surface, i.e. silica gel. The elimination of the process step of depositing tris(4,7-diphenyl-10-phenanthroline) ruthenium dichloride pentahydrate on silica gel greatly facilitated the commercialization of a new line of blood culture products.

In practice, a fluorophore stock solution is prepared by dissolving tris (4,7-diphenyl-10-phenanthroline)ruthenium dichloride pentahydrate in a dispensing agent. The dispensing agent may be a hydroxyl functional organic or a hydroxyl functional silicone compound. When the dispensing agent is a hydroxyl functional silicone compound, the component has the formula $X_n R_{(3-n)} SiO(RXSiO)_m SiR_{(3-n)} X_n$ wherein R independently represents a $C_1$–$C_{20}$ hydrocarbon radical;

X independently represents a hydroxyl radical or an $R^1$ radical;

n is the number 1 or 2;

m is a number sufficient to provide a viscosity of about 1 to about 500 millipascal-seconds at a viscosity of 25° C.; and $R^1$ is an unsaturated aliphatic hydrocarbon optionally substituted with 1 to 20 carbon atoms.

Preferably, the dispensing agent is SI205, but other agents may also be used to deliver the ruthenium fluorophore into the silicone matrix.

Examples of other dispensing agents which may be used in the present invention include vinyl ether capped organic polyether (DVE-3) and alcohols, such as ethanol (EtOH) or undecenyl alcohol (UDOL).

The fluorophore stock solution is then added to an organosilicon polymer having an average of at least two silicon-bonded curing radicals per molecule thereof. The radicals are preferably selected from the group consisting of hydroxyl radicals and olefinic hydrocarbon radicals. The resulting mixture is added to an organohydrogensilicon compound which acts to cross-link the hydroxyl or olefinic hydrocarbon radicals and thus converts the liquid mixture into a "solid" elastomer.

The reaction proceeds best in the presence of a catalyst, which is preferably a platinum group metal containing catalyst. It is most preferably a platinum group metal containing catalyst. However, it will be apparent to a skilled individual that the catalyst is not limited to such a group and may include any conventional catalysts, even heating at elevated temperatures.

The present composition may also include a filler. Preferably, the filler is fumed silica.

The composition may also include an acid added in an amount sufficient to maintain a neutral pH of about 7.0. The addition of an acid improves oxygen sensitivity.

With the present one-part homogenous formulation, no settling of coated silica will occur while the dispensed sensors stand at ambient or room (about 25° C.) temperature before being cured. Room temperature pre-cure time is therefore, not restricted. Cure of the sensor can be accomplished at a temperature range of about 85–100° C. in about 8 to 16 hours.

Applicants' one-part homogenous formulation is a surprising discovery in view of the knowledge available at the time of this invention. Ruthenium dichloride pentahydrate ("Ru") dye does not dissolve in regular non-polar organic solvents such as hexane or toluene. Rather, it is known to dissolve in hydroxy functional solvents such as alcohols. Good solubility indicates an interaction or attraction between the solute and the solvent, which, in the present case, is Ru dye and the hydroxy group of an alcohol. It is also known that silica is a matrix of $SiO_2$ which always contains unreacted silanol groups (Si—OH) as impurities. Applicants' hypothesized that Ru dye could be transferred from an alcohol (ethanol) solution to the surface of silica because of interactions between the Ru dye and the silanol. Applicants noted that, SI205, which is only known to be useful as a dispersing agent, has silanol groups.

Surprisingly, Applicants discovered that it was possible to utilize SI205 as a solvent for Ru dye as well as a liquid silica to host Ru dye. The resulting invention significantly simplifies and improves the working process of compounding Ru dye into a silicone elastomer. Settling does not occur since the formulation is homogeneous.

The following examples illustrate certain preferred embodiments of the instant invention, but are not intended to be illustrative of all embodiments.

EXAMPLE 1

Homogenous Oxygen Sensor (HOS) Formulated with tris-(4,7-diphenyl-1,10-phenanthroline) ruthenium dichloride pentahydrate ("Ru") in SI205.

Ru is dissolved in Bayer SI205 before it is added to silicone used to form the sensor. More Bayer SI205 can be added directly to the sensor formulation to improve performance if needed. The performance of this sensor is described in Table 1: An optimum concentration of SI205 exists. Too much SI205 causes poor adhesion (entry 1,4 vs. 2,3,5) and also increases the cure time (entry 1 and 2).

TABLE 1

Examples of HOS prepared using Bayer SI205 as a Solvent

| Entry | 1 | 2 | 3 | 4 | 5 |
|---|---|---|---|---|---|
| Lot # | 7D6M1 | 7D6M6 | 7D6M8 | 7D6M9 | 7D6M10 |
| Sensor Fill weight (gm) | 2 | 2 | 2 | 2 | 2 |
| Sensor signal response to Air[1] | — | 0.149 | 0.166 | 0.213 | 0.192 |
| Sensor Signal Response to $N_2$[2] | — | 0.422 | 0.620 | 0.743 | 0.921 |
| Dynamic Range of Sensor[3] | — | 223 | 273 | 248 | 410 |
| Cure condition | 74° C./20 h | 54° C./95 h | 74° C./20 h | 74° C./24 h | 72° C./9 h |
| Cured Sensor Adhesion to glass btl | poor | good | good | marginal | good |
| SF201 (%) (silicone) | 62.40 | 80.25 | 76.24 | 69.80 | 77.92 |
| Pt cat. (%) (for curing) | 0.0105 | 0.0102 | 0.0083 | 0.0092 | 0.0055 |
| Ru Fluorophore (%) | 0.0060 | 0.0062 | 0.0073 | 0.0072 | 0.0097 |
| SI205 (%) | 26.31 | 9.27 | 13.28 | 19.33 | 11.69 |
| $TiO_2$ (%) (additive) | 0.26 | 0.27 | 0.32 | 0.33 | 0.29 |
| XL-1 (%) (crosslinker for curing) | 10.96 | 10.18 | 10.12 | 10.52 | 10.03 |

[1]Sensor Signal Response to Air is defined as the fluorescent output of a sensor in a sealed BACTEC ® vial containing air. The output is measured in a BACTEC 9000 series instrument.
[2]Sensor Signal Response to Nitrogen is defined as the fluorescent output of a sensor in a sealed BACTEC ® vial containing nitrogen. The output is measured in a BACTEC 9000 series instrument.
[3]Dynamic Range = (Sensor response to Nitrogen − Sensor response to Air) (sensor response to air) × 100.

EXAMPLE 2

Oxygen Sensor Formulations Using Various Solvents to Achieve a In-Situ Coating Process A Ru stock solution was prepared by dissolving Ru in a delivery solvent such as alcohols or SI205. The stock solution was then added (see columns: solvent % & Fluo PPM) into silicone and fumed silica. Silica was thus coated with Ru in situ upon mixing. Due to the smaller particle size and lower density, the silica will remain in suspension during processing which is in contract to the previous heterogeneous technology where phase separation was observed during processing.

TABLE 2

Examples of HOS using various solvents

| ID 557- | Deliv. solv. | solv % | Fluo ppm | Silica % | TiO$_2$ % | Bro. pgmt | Air Response | N$_2$ Response | Dynamic Range |
|---|---|---|---|---|---|---|---|---|---|
| 28-1 | EtOH | 0.20 | 80 | 1.3 | 0.3 | 0 | 0.46 | 0.66 | 43 |
| 17-1 | EtOH | 0.83 | 83 | 1.3 | 0.4 | 0 | 0.42 | 1.61 | 263 |
| 22-1 | EtOH | 0.83 | 83 | 1.3 | 0.4 | 160 | 0.19 | 0.63 | 231 |
| 31-1 | UDOL | 0.83 | 83 | 1.3 | 0.4 | 0 | 0.45 | 1.07 | 137 |
| 31-.5 | UDOL | 0.42 | 42 | 0.7 | 0.4 | 0 | 0.27 | 0.60 | 122 |
| 33-1 | UDOL | 0.66 | 66 | 1.0 | 0.4 | 0 | 0.43 | 1.15 | 167 |
| 33-2 | UDOL | 0.55 | 55 | 0.8 | 0.4 | 0 | 0.40 | 1.04 | 160 |
| 34-2 | SI205 | 0.69 | 69 | 1.3 | 0.5 | 0 | 0.30 | 1.37 | 356 |
| 34-3 | SI205 | 0.35 | 69 | 1.3 | 0.5 | 0 | 0.31 | 1.19 | 284 |

UDOL: Undecenyl alcohol
Silica: Degussa R812 fumed silica
Brown Pgmt: Same pgmt used in Sensor I. Purpose of adding pgmt was to block a portion of the signal to depress air signal.

EXAMPLE 3

Process To Improve Sensor Adhesion

To improve lot-to-lot adhesion variation on the Ru/SI205/Silica formulation (shown at Table 5, cured at 73° C./15 hr), cure temperature was increased to 83° C. Several pilot lots were produced with formulations at higher cure temperature. Adhesion was acceptable. These studies show that adhesion can be improved with increased cure temperature.

TABLE 3

Examples of HOS Prepared with Higher Temperature Cure

| Sample ID | Polymer lot | Cure Temp./Time | Adhesion Test Results |
|---|---|---|---|
| 557-66-L | Lab PPG 152772 | 74° C./15 hr | Good |
| 557-66-L | Lab PPG 152772 | 83° C./15 hr | Good |
| 557-66-M | Mfg ctrl 12E6063 | 74° C./15 hr | Poor |
| 557-66-M | Mfg ctrl 12E6063 | 83° C./15 hr | Good |

EXAMPLE 4

Examples of HOS Prepared by the Addition of Acetic Acid to the Sensor Formulation to Improve Consistency of Response to Oxygen HOS sensor formulated with 11% SI205 (UCI/(without HOAc) formulation) suffered inconsistency while different lot of raw material, especially SI205, was used. Analytical data sheet of the SI205 agent showed the lot contained more ammonia (40 PPM) resulted compressed DR. The compressed DR sensor had higher starting signal and normal nitrogen signal (lot 7L6M1 and 7L6M12). By adding acetic acid (200 PPM) into formulations with SI205 contained either 40 PPM or) PPM of ammonia resulted identical to normal performance (lot 7L6M14, 16). This result led to the final formulation which required 200 ppm acetic acid added to the "UCI" formulation (see Table 6). The addition of acetic acid at 200 ppm produces sensors with consistent response to oxygen.

TABLE 4

Examples of HOS Prepared Using Acetic Acid

| Lot # | SI205 lot #* | HOAc | DFM, Air | DFM, N$_2$ | DFM, DR |
|---|---|---|---|---|---|
| 7L6M1 | 300F6062 | none | ~0.7 | ~1.1 | ~0.57 |
| 7L6M12 | 300F6062 | none | ~0.7 | ~1.1 | ~0.57 |
| 7L6M14 | 51217M | 200 ppm | 0.333 | 1.081 | 224 |
| 7L6M16 | 300F6062 | 200 ppm | 0.336 | 1.001 | 198 |

*lot 300F6062 contained 40 PPM ammonia
lot 51217M contained 0 PPM ammonia

TABLE 5

| | parts | wt % |
|---|---|---|
| Ru Stock Soln | | |
| Ru Complex | 1 | 1 |
| SI205 | 99 | 99 |
| total | 100 | 100 |
| HOS with silica | | |
| SF201 | 49.51 | 86.01271 |
| 1% Pt, PS925/201 | 0.6 | 1.044477 |
| (Pt catalyst.) | 0.006 | (0.010445) |
| PS925 | 0.006 | (0.010445) |
| Ru/SI205 Stock Solution | 0.385 | 0.670206 |
| (SI205) | 0.38115 | (0.663504) |
| (Ru | 0.00385 | (0.006702) |
| Fumed Silica | 0.75 | 1.305597 |
| TiO2 (titanium dioxide) | 0.3 | 0.522239 |
| XL-1 Silicone Crosslinker | 6 | 10.44477 |
| Total | 57.445 | 100 |

TABLE 6

| | parts | wt % |
|---|---|---|
| Ru Stock Solution | | |
| Ru | 0.25 | 0.25 |
| SI205 | 99.75 | 99.75 |
| total | 100 | 100 |
| HOS 1-part formulation | | |
| SF201 | 162.48 | 77.9568474 |
| 1% Pt catalyst/SI205 | 1.78 | 0.85403242 |

TABLE 6-continued

|  | parts | wt % |
| --- | --- | --- |
| (Pt cat.) | 0.0178 | (0.00854032) |
| Ru Stock | 8.13 | 3.90072113 |
| (Ru cplx) | 0.020325 | (0.0097518) |
| SI205 | 14.488 | 6.95124818 |
| (total SI205) | 24.359875 | (11.6877096) |
| TiO2 | 0.6 | 0.2878761 |
| HOAc | 0.045 | 0.02159071 |
| XL-1 (silicone Crosslinker | 20.9 | 10.0276841 |
| Total | 208.423 | 100 |

It will be apparent to a skilled individual that many modifications and variations of this invention as hereinabove set forth may be made without departing from its spirit and scope. The specific embodiments as described are given only by way of example and the invention is not intended to be limited thereby.

We claim:

1. A composition for detecting the growth of respiring microorganisms in a sample which comprises:
   (a) tris (4,7-diphenyl-10-phenanthroline)ruthenium dichloride pentahydrate;
   (b) a hydroxyl functional organic;
   (c) an organosilicon polymer;
   (d) an organohydrogensilicon compound; and
   (e) a catalyst.

2. The composition according to claim 1 further comprising a filler.

3. The composition according to claim 2 wherein said filler is fumed silica.

4. The composition according to claim 1 wherein said catalyst is a platinum group metal-containing catalyst.

5. A composition for detecting the growth of respiring microorganisms in a sample which comprises:
   (a) tris(4,7-diphenyl-10-phenanthroline)ruthenium dichloride pentahydrate;
   (b) a hydroxyl functional silicone compound;
   (c) an organosilicon polymer;
   (d) an organohydrogensilicon compound; and
   (e) a catalyst.

6. The composition according to claim 5 further comprising a filler.

7. The composition according to claim 6 wherein said filler is fumed silica.

8. The composition according to claim 5 further comprising an acid added in an amount sufficient to maintain a neutral pH of about 7.0 of said composition.

9. The composition according to claim 5 wherein said hydroxyl functional silicone compound has the formula $X_n R_{(3-n)} SiO(RXSiO)_m SiR_{(3-n)} X_n$ wherein R independently represents a $C_1$–$C_{20}$ hydrocarbon radical;

X independently represents a hydroxyl radical or an $R^1$ radical;

n is the number 1 or 2;

m is a number sufficient to provide a viscosity of about 1 to about 500 millipascal-seconds at a viscosity of 25° C.; and $R^1$ is an unsaturated aliphatic hydrocarbon optionally substituted with 1 to 20 carbon atoms.

10. The composition according to claim 5 wherein said catalyst is a platinum group metal-containing catalyst.

11. A method for preparing a composition for detecting the growth of respiring microorganisms in a sample which comprises the steps of:
   (i) forming a solution of tris(4,7-diphenyl-10-phenanthroline)ruthenium dichloride pentahydrate and a hydroxyl functional group containing compound;
   (ii) adding an organosilicon polymer to said solution forming a mixture;
   (iii) adding an organohydrogensilicon compound to said mixture in the presence of a catalyst forming an elastomer; and
   (iv) adding a filler to said elastomer.

12. The method of claim 11 wherein said hydroxyl functional group containing compound is a hydroxyl functional organic.

13. The method of claim 12 wherein said filler is fumed silica.

14. The method of claim 13 wherein said catalyst is a platinum group metal-containing catalyst.

15. The method of claim 11 wherein said hydroxyl functional group containing compound is a hydroxyl functional silicone compound.

16. The method of claim 15 wherein said filler is funed silica.

17. The method of claim 16 further comprising an acid added in an amount sufficient to maintain a neutral pH of about 7.0 of said composition.

18. The method of claim 17 wherein said hydroxyl functional silicone compound has the formula $X_n R_{(3-n)} SiO (RXSiO)_m SiR_{(3-n)} X_n$ wherein R independently represents a $C_1$–$C_{20}$ hydrocarbon radical;

X independently represents a hydroxyl radical or an $R^1$ radical;

n is the number 1 or 2;

m is a number sufficient to provide a viscosity of about 1 to about 500 millipascal-seconds at a viscosity of 25° C.; and $R^1$ is an unsaturated aliphatic hydrocarbon optionally substituted with 1 to 20 carbon atoms.

19. The method of claim 18 wherein said catalyst is a platinum group metal-containing catalyst.

20. A composition for detecting the growth of respiring microorganisms in a sample wherein said composition comprises tris-(4,7-diphenyl-10-phenanthroline)ruthenium dichloride pentahydrate dissolved in a silanol functional silicon polymer forming a solution and wherein said solution is incorporated into a liquid silicone polymer.

* * * * *